United States Patent
Pacheco

(10) Patent No.: US 8,277,461 B2
(45) Date of Patent: Oct. 2, 2012

(54) METHODS FOR DETERMINING PEDICLE BASE CIRCUMFERENCE, PEDICLE ISTHMUS AND CENTER OF THE PEDICLE ISTHMUS FOR PEDICLE SCREW OR INSTRUMENT PLACEMENT IN SPINAL SURGERY

(75) Inventor: Hector O. Pacheco, El Paso, TX (US)

(73) Assignee: Leucadia 6, LLC, El Paso, TX (US)

( * ) Notice: Subject to any disclaimer, the term of this patent is extended or adjusted under 35 U.S.C. 154(b) by 1206 days.

(21) Appl. No.: 11/657,119

(22) Filed: Jan. 24, 2007

(65) Prior Publication Data

US 2007/0232960 A1   Oct. 4, 2007

Related U.S. Application Data

(60) Provisional application No. 60/761,365, filed on Jan. 24, 2006.

(51) Int. Cl.
*A61B 17/58* (2006.01)
*A61B 17/60* (2006.01)

(52) U.S. Cl. .......... 606/102; 606/91; 606/104; 382/128; 600/587; 600/411; 600/424

(58) Field of Classification Search .............. 606/587, 606/594, 104, 130; 382/128; 600/407, 411, 600/587, 594, 424
See application file for complete search history.

(56) References Cited

U.S. PATENT DOCUMENTS

| | | | |
|---|---|---|---|
| 5,291,537 A * | 3/1994 | Mazess | 378/54 |
| 5,351,404 A | 10/1994 | Smith | |
| 6,259,806 B1 * | 7/2001 | Green | 382/128 |
| 6,282,437 B1 | 8/2001 | Franck et al. | |
| 6,351,662 B1 | 2/2002 | Franck et al. | |
| 6,470,207 B1 | 10/2002 | Simon et al. | |
| 6,477,400 B1 | 11/2002 | Barrick | |
| 6,484,044 B1 | 11/2002 | Lilienfeld-Toal | |
| 6,490,467 B1 | 12/2002 | Bucholz et al. | |
| 6,490,475 B1 | 12/2002 | Seeley et al. | |
| 6,529,765 B1 | 3/2003 | Franck et al. | |
| 6,546,277 B1 | 4/2003 | Franck et al. | |
| 6,697,664 B2 | 2/2004 | Kienzle, III et al. | |
| 6,741,883 B2 | 5/2004 | Gildenberg | |
| 6,792,071 B2 * | 9/2004 | Dewaele | 378/62 |
| 7,149,120 B2 * | 12/2006 | Lee et al. | 365/185.22 |
| 7,194,120 B2 * | 3/2007 | Wicker et al. | 382/128 |
| 7,235,076 B2 * | 6/2007 | Pacheco | 606/86 A |
| 2002/0161368 A1 | 10/2002 | Foley et al. | |
| 2003/0187348 A1 * | 10/2003 | Goodwin | 600/424 |
| 2004/0092932 A1 | 5/2004 | Aubin et al. | |

(Continued)

*Primary Examiner* — Thomas Barrett
*Assistant Examiner* — Matthew Lawson
(74) *Attorney, Agent, or Firm* — Nixon & Vanderhye PC

(57) ABSTRACT

A method of determining the pedicle base circumference and the pedicle isthmus to facilitate screw placement in a pedicle of a vertebral body during spinal surgery, comprising providing a series of first lines tangential to the outer cortical surface of the vertebral body in and near the pedicle on a transverse section from a three-dimensional image of the vertebral body, providing a series of second lines extending through the vertebral body in and near the pedicle thereof in perpendicular relation to the series of first lines, identifying the pedicle base circumference as the areas of the outer cortical surface where adjacent second lines are at the greatest angle with respect to one another, and identifying the pedicle isthmus as the areas of the outer cortical surface where the second lines that are opposed to each other are closest to being parallel to one another.

4 Claims, 4 Drawing Sheets

U.S. PATENT DOCUMENTS

| | | | |
|---|---|---|---|
| 2004/0240715 A1* | 12/2004 | Wicker et al. | 382/128 |
| 2005/0020942 A1* | 1/2005 | Wada et al. | 600/594 |
| 2005/0101970 A1* | 5/2005 | Rosenberg | 606/130 |
| 2005/0192575 A1* | 9/2005 | Pacheco | 606/61 |
| 2005/0267354 A1* | 12/2005 | Marquart et al. | 600/411 |
| 2006/0058616 A1* | 3/2006 | Marquart et al. | 600/407 |
| 2006/0235338 A1* | 10/2006 | Pacheco | 600/587 |

* cited by examiner

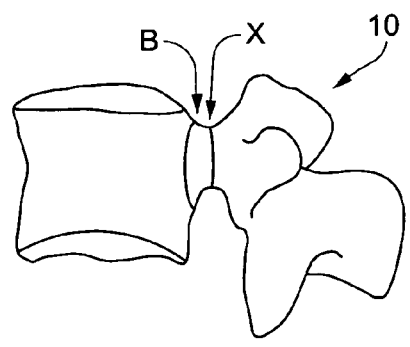
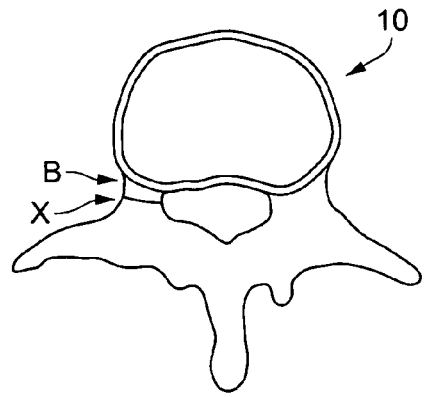
FIGURE 1A  FIGURE 1B
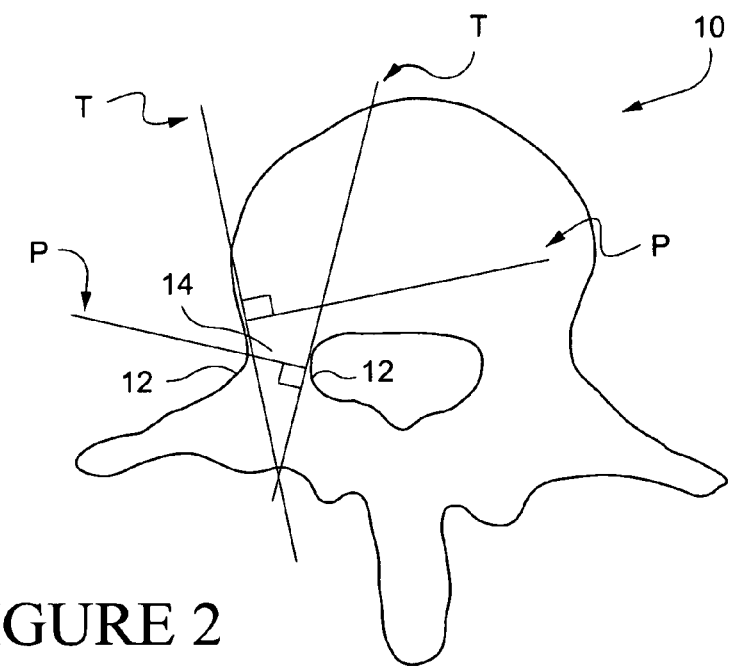
FIGURE 2

METHODS FOR DETERMINING PEDICLE BASE CIRCUMFERENCE, PEDICLE ISTHMUS AND CENTER OF THE PEDICLE ISTHMUS FOR PEDICLE SCREW OR INSTRUMENT PLACEMENT IN SPINAL SURGERY

This application claims the benefit of U.S. Provisional Patent Application No. 60/761,365 filed on Jan. 24, 2006.

FIELD OF THE INVENTION

The present invention relates generally to the field of spinal surgery, to computerized or automated methods for the accurate placement of pedicle screws or instruments in spinal surgery and, more particularly, to methods for determining pedicle base circumference, pedicle isthmus and the center of the pedicle isthmus.

BACKGROUND OF THE INVENTION

Placement of screws into the human spine is a common surgical procedure to allow for a multitude of spinal surgeries to be performed. Screws are typically placed into the pedicles of individual vertebra in the lumbar and sacral spine. Given their biomechanical advantages over other modes of fixation, surgeons are expanding the areas of the spine in which pedicle screws are placed. However, adjacent to the spine are numerous vital structures and organs, in particular the cervical and thoracic spine regions, which have very low tolerance for surgically created injuries that may ultimately lead to significant morbidity and/or mortality. For this reason the majority of research focus on placement of pedicle screws is centered on improving accuracy to maintain a screw within a bony (intraosseous) environment.

Image guided systems are evolving which are increasingly user friendly to assist a surgeon in accurately placing a screw. The critical parameters for placing a pedicle screw into the human spine are diameter, length, trajectory and then actual placement of the screw. To date many of the image guidance systems allow for manual determination of these parameters to improve a surgeon's manual performance in screw placement. Up to the present time, no system is available which will automatically determine ideal pedicle screw diameter, length and trajectory for accurate placement of pedicle screws. The present invention provides this capability akin to a pilot who flies an airplane with computer controlled aviation capabilities, and allows for placement of pedicle screws using either an open or percutaneous technique.

Patent Application Publication No. US 2004/0240715 A1, published on Dec. 2, 2004, relates to methods and computer systems for determining the placement of pedicle screws in spinal surgery. It discloses a method wherein the minimum pedicle diameter is first established for determining the optimum screw trajectory and then the maximum screw diameter and length using the optimum trajectory for each pedicle. Two dimensional transverse slice data is stacked to form three dimensional data points to determine optimum trajectory by linear least squares solution to fit the data, requiring the solution to go through the overall minimum transverse pedicle widths. A disadvantage of this method is that it allows for eccentric trajectory determination, particularly for distorted pedicle anatomy, with consequent smaller maximum diameter and length screw determinations resulting in biomechanically inferior constructions. In contrast, the new and improved method of the present invention always places the trajectory concentrically through the pedicle by the determination of optimum trajectory by using the center point of the smallest cross sectional area (isthmus) and projecting with a computer a line normal to this circumscribed area in opposite directions, as described more particularly hereinafter. The new and improved methods of the present invention allow for maximum screw diameter and length determinations for intraosseous placement.

In Patent Application Publication No. 2005/0192575-AL, dated Sep. 1, 2005, relating to methodology for the determination of ideal pedicle screw diameter, length and trajectory there is a description of the transitional interface where the pedicle is joined to the vertebral body. This transitional interface describes the pedicle base circumference (B) which is identified radiographically on anteroposterior radiographic imaging as a round like cortical density seen on the cephalad lateral aspect of the vertebral body. An essential feature of this pedicle base circumference is that it is different from the pedicle isthmus (X, the narrowest region within a pedicle), but can on occasion be the same. The pedicle isthmus is the rate limiting step to maximizing the largest diameter pedicle screw without causing a breach of the cortical wall. To maximize the diameter of the pedicle screw within any given pedicle the pedicle isthmus must be determined. Subsequently, the center of the pedicle isthmus allows determination of the ideal trajectory to allow for concentric pedicle screw placement along the ideal trajectory.

The present application is directed to new and improved methods for determining the pedicle base circumference, pedicle isthmus and center of the pedicle isthmus.

SUMMARY OF THE INVENTION

In accordance with the methods of the present invention, serial stacked images in any plane are obtained of the vertebral body in any suitable manner. These images are then reconstructed to obtain a dimensionally true three-dimensional rendering of the vertebral body. The pedicle base circumference and pedicle isthmus are depicted in three-dimensional and two-dimensional images.

Once a true three-dimensional rendering of a vertebral body is obtained, it is then sectioned in a transverse plane to visualize and obtain an outer cortical shell. A series of first lines are then drawn tangentially along the outer cortical surface. A series of second lines are then drawn perpendicular to the tangential lines lying on the outer cortical surface, with the second lines lying within the vertebral body.

In the area of the pedicle and its transition into the vertebral body, the second lines will define the pedicle base circumference and pedicle isthmus. Specifically, the pedicle base circumference is defined as the region in which the adjacent second lines are at the greatest angle, non-linear or discordant, to one another. The pedicle isthmus is defined as the region in which the opposing second lines are most parallel to one another. Infinitesimal points on the outer cortical surface are utilized for the placement of the first tangential surface lines and their respective second perpendicular lines.

Once the pedicle isthmus is defined, it is then necessary to define the center of the pedicle isthmus to allow for concentric trajectory determination and pedicle cylinder building. Most pedicles are conceptualized as being cylindrical, although many pedicles have oval or irregular volumes. As such, it is essential to accurately determine the center of these pedicles. The method of the present invention utilizes the cross-sectional area defined by the pedicle isthmus and then identifies the center of this cross-sectional area as that point which lies at the intersection of two lines derived from the centers of infinitesimal orthogonal second perpendicular lines from the outer cortical surface. This methodology allows for pedicle isthmus center determination irrespective of pedicle configuration.

BRIEF DESCRIPTION OF THE DRAWINGS

FIG. 1A is a schematic drawing of a sagittal image of a vertebral body;

FIG. 1B is a schematic drawing of a transverse image of a vertebral body;

FIG. 2 is a schematic drawing of the vertebral body shown in FIG. 1B;

DESCRIPTION OF THE PREFERRED EMBODIMENTS

Pedicle Base Circumference and Pedicle Isthmus Determination

In accordance with the methods of the present invention, serial stacked images in any plane are obtained of the vertebral body 10 in any suitable manner. These images then are reconstructed to obtain a dimensionally true three-dimensional rendering of the vertebral body 10. The pedicle base circumference B and pedicle isthmus X are depicted in the three-dimensional and two-dimensional images as shown schematically in FIGS. 1A and 1B.

Once a true three-dimensional rendering of the vertebral body 10 is obtained, it is sectioned in a transverse plane to visualize and obtain an outer cortical shell. A series of first lines T are then drawn tangentially to and along the outer cortical surface 12. A series of second lines P are then drawn perpendicular to the first lines T lying on the outer cortical surface 12 with the second lines P lying within the vertebral body 10. This is illustrated in FIG. 2 with respect to only two first tangential lines T and two second perpendicular lines P as an illustrative example.

Figure 3:
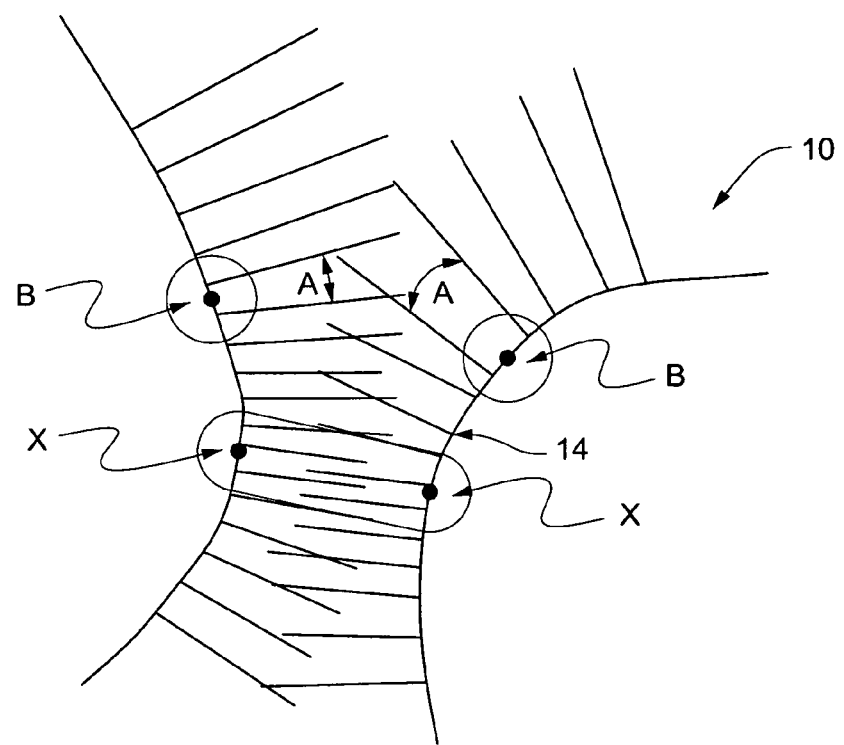
FIG. 3 is a schematic view of the pedicle portion of the vertebral body shown in FIG. 2, showing infinitesimal tangential surface lines and their respective perpendicular lines as shown in FIG. 2.

In the area of the pedicle 14 and its transition into the vertebral body 10, the series of second perpendicular lines P will define the pedicle base circumference B and pedicle isthmus X. Specifically, the pedicle base circumference B is defined as that region in which the adjacent second perpendicular lines P are at the greatest angle A, nonlinear or discordant to one another. Conversely, the pedicle isthmus X is the region in which opposing second perpendicular lines P are most parallel to one another. Infinitesimal points on the outer cortical surface are utilized for placement of the first tangential lines T and their respective second perpendicular lines P. This is illustrated schematically in FIG. 3.

Figure 4A:
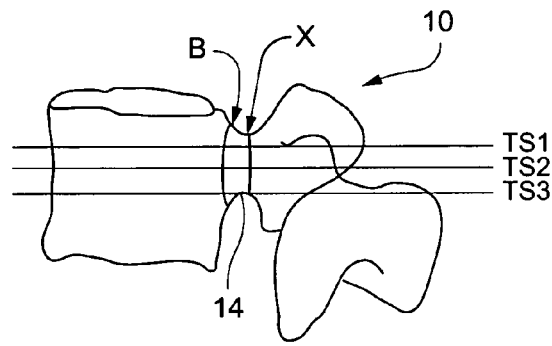
FIG. 4A is a schematic drawing of a sagittal image of the vertebral body showing the location of the pedicle base circumference and pedicle isthmus determined in accordance with the methods of the present invention.
Figure 4B:
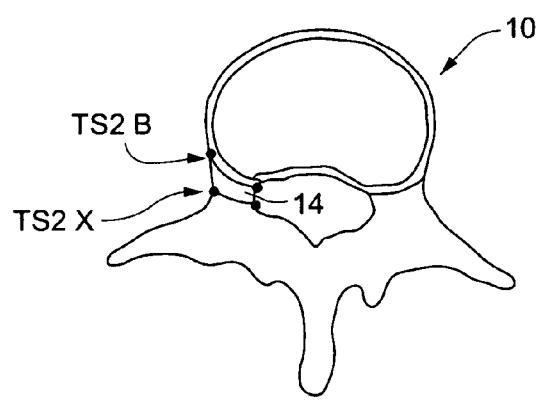
FIG. 4B is a schematic drawing of a transverse image of the vertebral body showing the pedicle base circumference and the pedicle isthmus determined in accordance with the methods of the present invention.
Figure 4C:
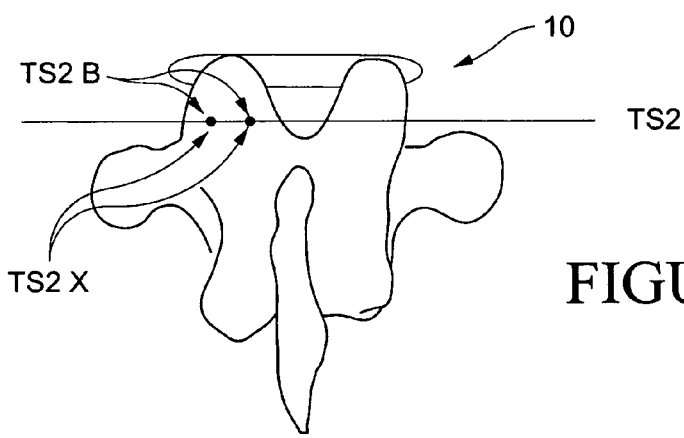
FIG. 4C is a schematic drawing of a coronal image of the vertebral body showing the location of the pedicle base circumference and pedicle isthmus determined in accordance with the methods of the present invention.

The points from infinite transverse sections (TS1, TS2, TS3 . . . ) defining the pedicle base B and pedicle isthmus X are then collated to determine the anatomical three-dimensional location of the pedicle base circumference B and pedicle isthmus X, as shown in FIGS. 4A, 4B and 4C. FIGS. 4B and 4C show the transverse section TS2 through the center of the pedicle 14 and its corresponding point on a transverse and coronal projection, respectively.

Pedicle Isthmus Center Determination

Figure 5A:
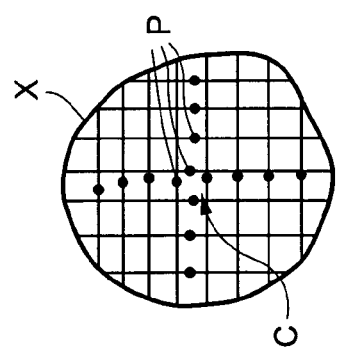
FIG. 5A is a schematic cross-section of a pedicle isthmus illustrating the center thereof as determined in accordance with the methods of the present invention.
Figure 5B:
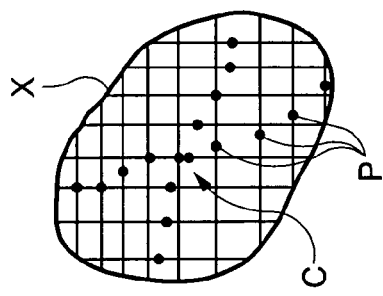
FIG. 5B is a schematic view of the cross-section of a pedicle isthmus having an irregular shape showing the center thereof as determined in accordance with the methods of the present invention.
Figure 5C:
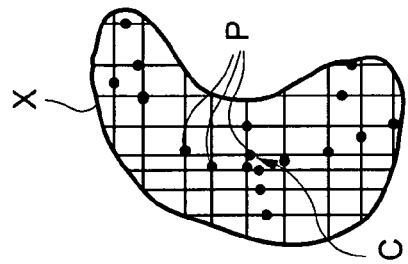
FIG. 5C is a schematic view of a pedicle isthmus cross-section having a different irregular shape showing the center thereof as determined in accordance with the methods of the present invention.

Once the pedicle isthmus X is defined, the center of the pedicle isthmus C must be further defined. This is necessary to allow for concentric trajectory determination and pedicle cylinder building. Most pedicles are conceptualized as being cylindrical; however, many pedicles have oval or irregular volumes. As such, it is essential to determine the center of these pedicles. The new and improved method of the present invention utilizes the cross-sectional area defined by the pedicle isthmus X and then identifies the center C of the cross-sectional area as being that point which lies at the intersection of two lines derived from the centers of the infinitesimal orthogonal second perpendicular lines P as illustrated in FIGS. 5A, 5B and 5C. This methodology allows for pedicle isthmus center determination irrespective of different pedicle configurations as shown in FIGS. 5A, 5B and 5C.

It will be readily seen that the methods of the present invention provide for simple and reliable determination of pedicle base circumference, pedicle isthmus and the center of the isthmus to provide for concentric pedicle screw placement along the ideal trajectory. These methods can be effected in any suitable manner, such as visual imaging through the use of a computer or the like, or manually from two-dimensional sections.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method of determining the pedicle base circumference and the pedicle isthmus for enabling optimum screw or instrument placement in a pedicle of a vertebral body during spinal surgery, comprising:

using computer imaging apparatus to create a three-dimensional image of the vertebral body, using computer imaging apparatus to create an image of the outer cortical shell of the vertebral body by taking a section of the three-dimensional image in a transverse plane;

using computer imaging apparatus to provide on the transverse section a series of first lines tangential to the outer cortical surface of the vertebral body in and near the pedicle;

using computer imaging apparatus to provide a series of second lines substantially perpendicular to the series of first lines, said second lines extending through the vertebral body in and near the pedicle thereof;

using computer imaging apparatus to identify the pedicle base circumference as the areas of the outer cortical surface where adjacent second lines are of the greatest angle with respect to one another; and using computer imaging apparatus to identify the pedicle isthmus as the areas of the outer cortical surface where said second lines that are opposed to each other are closest to being parallel to one another.

2. The method of claim 1 wherein infinitesimal points are utilized on the outer cortical surface for the placement of said first lines and said second lines.

3. The method of claim 2 wherein anatomical three-dimensional locations of the pedicle base circumference and pedicle isthmus are determined by collating infinite transverse sections defining the pedicle base circumference and pedicle isthmus.

4. The method of claim 1 further comprising identifying a center of the pedicle isthmus from a cross-section thereof as the intersection of two lines derived from the centers of infinitesimal orthogonal second lines extending from the outer cortical surface.

* * * * *